United States Patent
Brodmann et al.

(10) Patent No.: US 10,180,316 B2
(45) Date of Patent: Jan. 15, 2019

(54) METHOD AND DEVICE FOR THE CONTACTLESS ASSESSMENT OF THE SURFACE QUALITY OF A WAFER

(71) Applicant: Brodmann Technologies GmbH, Bischweier (DE)

(72) Inventors: Rainer Brodmann, Bischweier (DE); Boris Brodmann, Karlsruhe (DE)

(73) Assignee: Brodmann Technologies GmbH, Bischweier (DE)

( * ) Notice: Subject to any disclaimer, the term of this patent is extended or adjusted under 35 U.S.C. 154(b) by 0 days.

(21) Appl. No.: 15/753,660

(22) PCT Filed: Aug. 25, 2016

(86) PCT No.: PCT/EP2016/070033
§ 371 (c)(1),
(2) Date: Feb. 20, 2018

(87) PCT Pub. No.: WO2017/032819
PCT Pub. Date: Mar. 2, 2017

(65) Prior Publication Data
US 2018/0245911 A1     Aug. 30, 2018

(30) Foreign Application Priority Data
Aug. 25, 2015  (DE) ......................... 10 2015 114 065

(51) Int. Cl.
*G01B 11/30* (2006.01)
*G01N 21/47* (2006.01)
(Continued)

(52) U.S. Cl.
CPC .......... *G01B 11/303* (2013.01); *B23Q 17/003* (2013.01); *B23Q 17/20* (2013.01);
(Continued)

(58) Field of Classification Search
CPC .... G01B 11/303; B23Q 17/003; B23Q 17/20; G01N 21/4738; G01N 21/9501; G01N 2021/4723
(Continued)

(56) References Cited

U.S. PATENT DOCUMENTS

2007/0229833 A1  10/2007  Rosencwaig
2012/0092656 A1   4/2012  Nakao

FOREIGN PATENT DOCUMENTS

DE          3503858 A1   8/1986
DE          3037622 C2   2/1987
(Continued)

OTHER PUBLICATIONS

Rainer Brodmann et al., Kenngroβen der Mikrostruktur definiert, http://vda-qmc.de/fileadmin/redakteur/presse/Kenngroessen_der_Mikrostruktur_definiert.pdf, QZ, Jul. 1, 2008, pp. 46-49.
(Continued)

*Primary Examiner* — Tri T Ton
(74) *Attorney, Agent, or Firm* — McGarry Bair PC

(57) ABSTRACT

A method and a device for contactless assessment of the surface quality of a workpiece (W) according to the angle-resolved scattered light measuring technique comprises an optical sensor (10) which illuminates a measuring spot (14). The intensity of the radiation which is reflected back is detected by means of a line sensor (16), and an intensity characteristic value (Ig) is determined therefrom. A horizontal initial rotation angle (θ) at which the intensity characteristic value is at a maximum is determined. In a measuring operating mode, surface characteristic values are calculated taking into account this initial rotational angle (θ). The measuring method is defined by extremely high lateral and vertical spatial resolution, extending into the subnanometer range, and by a high measuring speed.

15 Claims, 12 Drawing Sheets

(51) Int. Cl.
  *G01N 21/95* (2006.01)
  *B23Q 17/00* (2006.01)
  *B23Q 17/20* (2006.01)

(52) U.S. Cl.
  CPC ..... *G01N 21/4738* (2013.01); *G01N 21/9501* (2013.01); *G01N 2021/4723* (2013.01)

(58) Field of Classification Search
  USPC .................................................. 356/600–640
  See application file for complete search history.

(56) References Cited

FOREIGN PATENT DOCUMENTS

| | | |
|---|---|---|
| DE | 3304780 C2 | 9/1989 |
| DE | 4408226 A1 | 9/1995 |
| DE | 102012005417 B4 | 10/2013 |
| EP | 2657686 A1 | 4/2012 |

OTHER PUBLICATIONS

VDA 2009. Geometrische Produktspezifikation. Oberflächenbeschaffenheit. Winkelaufgelöste Streulichtmesstechnik. Definition, Kenngrößen und Anwendung. Jul. 2010.

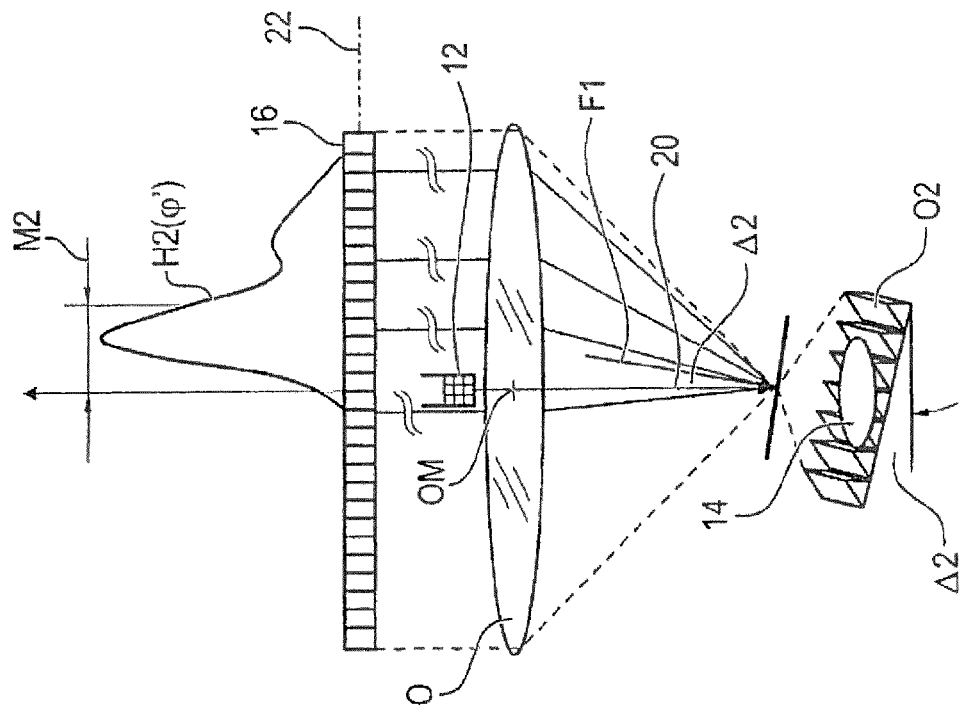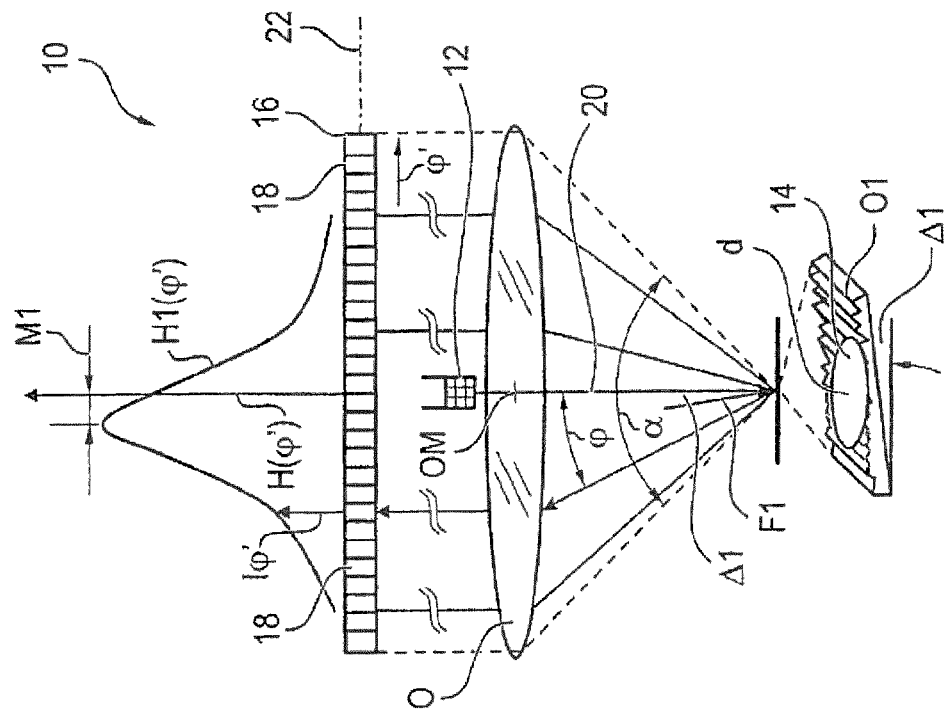
FIG. 1

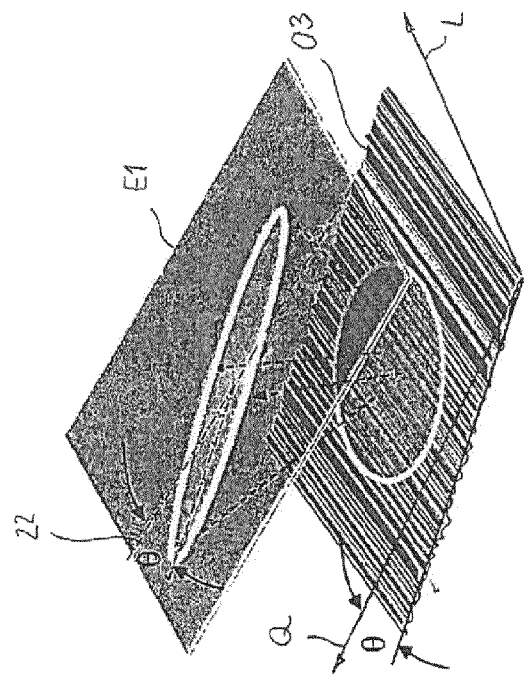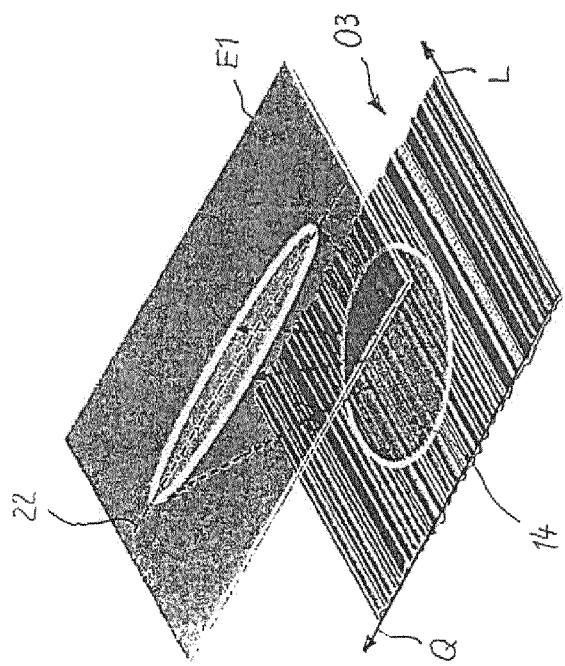
Fig. 4

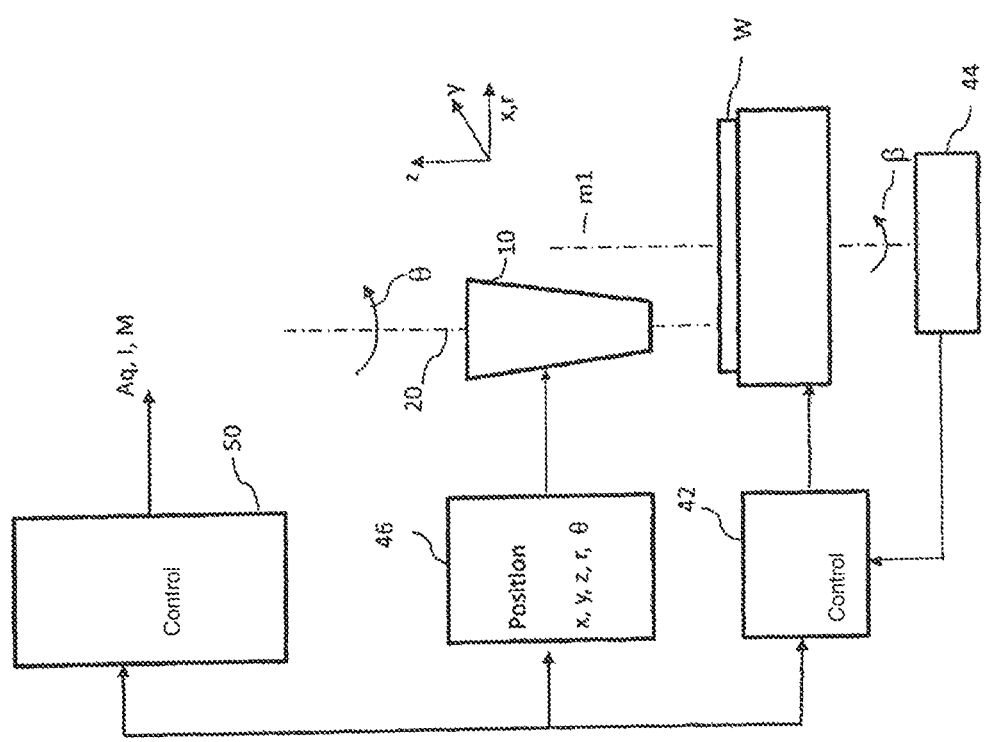

METHOD AND DEVICE FOR THE CONTACTLESS ASSESSMENT OF THE SURFACE QUALITY OF A WAFER

This application is a National Phase application of International Application No. PCT/EP2016/070033, filed Aug. 25, 2016, which claims the benefit of German Application DE 10 2015 114 065.9, filed on Aug. 25, 2015, both which are incorporated herein in in their entireties.

The invention relates to a method for the contactless assessment of the surface quality of a disk-shaped, fine-machined workpiece, in particular a wafer, according to the angle-resolved scattered light measuring technique, in which an optical sensor emits a beam of rays with defined intensity distribution onto that surface of the workpiece which is to be assessed and illuminates a measuring spot, wherein the reflected intensity of the radiation is detected by means of a line sensor with a discrete number of photodetectors in a defined angular range and at least one characteristic value with respect to the surface quality is calculated from the detected intensity. Further, the invention relates to a device for implementing the method.

The angle-resolved scattered light measuring technique with associated sensor is described in every detail in the VDA recommendation VDA 2009 from July 2010 (VDA Verband der Automobilindustrie [German Association of the Automotive Industry]). Due to the ruggedness of the method and the high measuring speed, this scattered light measuring technique is suitable both for 100% online surveillance of a process, and specifically for the contactless measurement of the roughness transverse to the machining direction (cross roughness) and along the machining direction (longitudinal roughness) as well as for shape and waviness measurement. Here, the angular distribution of the surface of a fine-machined surface is measured via re-scattered light. Therefrom, both characteristic values for the structure of the surface and shape features such as flatness, roundness, waviness, chatter marks, etc. can be calculated. As a characteristic value for the assessment of the quality of a surface, for example the variance of the scattered light distribution Aq can be used as a measure for the microstructure of the surface.

Further, the scattered light measuring technique is described in EP 2 657 686 A1 and the publication "Kenngrößen der Mikrostruktur definiert", Rainer Brodmann et al., QZ volume 53 (2008), 7, pages 46-49. Depending on the orientation, the intensity distribution is detected by the scattered light sensor in the cross direction or the longitudinal direction with respect to the machining direction of the workpiece. From the distribution curve, statistic characteristic values containing information on the cross roughness or the longitudinal roughness can then be calculated. Here, the most important characteristic values are Aq and M, wherein M is the mean value of the distribution curve and thus the center of area of the distribution curve.

An important application is the assessment of the surface of disk-shaped workpieces, in particular of wafers. When producing ICs (integrated circuits) it is increasingly required to produce the individual ICs as thin as possible. The starting materials in the IC production are mostly silicon disks (wafers) having a diameter of 200 to 300 mm and a thickness of 500 to 725 µm. After production, the actual electronic hardware elements are located at a depth of only some µm, which means that 99% of the material is more or less useless. This relatively large thickness that is advantageous in the production process for the ICs is, on the other hand, disadvantageous with respect to a required cooling of the ICs from the back side if the ICs having a considerable overall thickness were to be used in an electronic device. For this reason, wafers are thinned from the unmachined backside by means of a grinding process prior to the removal of the ICs and their separation. This so-called back grinding of processed wafers is a standard method nowadays, wherein final thicknesses of less than 200 µm are obtained. The tendency is to reduce the thickness by back grinding up into the 50 µm range. The thinner the wafer is ground, the more careful the machining has to be done, so that occurring grinding forces and the surface removal, in particular in the end phase of the machining shortly before reaching the target thickness, have no too high effects on the electronic circuit elements of the ICs located underneath. Here, the grinding forces should be distributed as homogeneously as possible and due to the process parameters to be kept within narrow limits (i.a. grinding wheel grain size, rotation speed and pressure of the grinding wheel) the surface roughness and the surface deformation (warpage, waviness etc.) on the entire wafer surface should be so little as possible and uniform. If this is not the case, then stress and microcracks can have a negative effect on the function of the ICs or destroy them. In the case of wafers with a thickness range of about 50 µm, the roughness should, for example, not exceed 1 to 3 nm Ra (mean roughness index). Often, after ultrafine grinding an additional CMP process step (CMP: chemical mechanical polishing or chemical mechanical planarisation) is implemented for further reduction of the roughness and the fine waviness.

In FIG. 2a, the basic principle for the back grinding is illustrated. A grinding wheel S that is formed as a cup wheel and is slightly tilted removes material from the surface of a wafer W on its back, wherein both the grinding wheel S and the wafer W rotate. Depending on the grinding level (rough, medium, fine and superfine), this grinding process leaves S-shaped grinding scratches and grinding grooves on the wafer W. These may still be visible up into the finest area of the surface, however in the case of super finishing these can hardly be seen with the bare eye. If even these processing traces are to be reduced still further, the CMP method is employed. In the case of this method illustrated in FIG. 2b, the wafer W is attached to the underside of a rotation unit RE and is rotated relative to a rotating polishing wheel PS which is applied to the rotary table DT. As a polishing agent a chemical emulsion E is applied, which further smoothes the wafer surface in a very careful manner. The roughness index Ra is reduced to considerably less than 1 nm. This also has positive effects on the form deviation and with respect to the nanotopography on the waviness.

For the quality assurance on such wafer workpieces, as far as the thickness and the warpage is concerned, there are measuring techniques introduced in the prior art which, with optical sensors, can also measure differences in the submicrometer range over the whole surface of the wafer. For measuring the roughness, there are methods in the prior art that perform a pointwise measurement of the roughness on the surface, for example at five selected points of the wafer surface. Here, inter alia, interferometrically operating measuring microscopes or atomic force microscopes (AFM) are used as measuring techniques. From the total surface of a wafer having a diameter of 300 mm, i.e. of 70650 mm$^2$, in the five-point-measurement with a measuring spot of 1 mm$^2$ each only a negligible fraction of the machined surface is assessed. An exact assessment of the entire surface of the wafer with respect to roughness, shape and the nanotopography, in particular waviness, would however be desirable.

From DE 44 08 226 A1, a measuring device for determining the roughness of the technical surface by evaluation of chromatic speckle patterns is known, which is based on the light scattering on rough surfaces. A surface section is illuminated by means of one or more ray bundles in a dichromatic or polychromatic manner, and the scattered light emitted from the rough surface is detected by means of a detector array and is stored as a grey level image in a data memory. This stored image is evaluated according to specific criteria, and roughness characteristic values are determined therefrom.

From DE 10 2012 005 417 B4, a device and a method for the angle-resolved scattered light measurement is known, in which a detector device detects at least two portions of a reflected light scattered on the surface. From the scattered portions of the light, a spectral power density is determined and roughness parameters are inferred therefrom.

It is the object of the invention to specify a method and a device for the contactless assessment of the surface quality of a disk-shaped workpiece, in which an extensive surface assessment with a high accuracy and a high scanning speed can take place.

This object is solved for a method according to the features of claim 1. Advantageous developments are specified in the dependent claims.

In the case of disk-shaped, fine-machined workpieces the roughness structure of the surface generally has a preferred direction. For example, in the case of wafers, there result S-shaped grinding grooves (see FIG. 2) due to a rotation of the grinding wheel in connection with the rotation of the wafer. On such anisotropic surfaces, a longitudinal roughness is defined in the direction of the grinding grooves and a cross roughness is defined transversely thereto. For forming a characteristic value with respect to the surface quality, it is now important to define the orientation of the optical sensor at a measuring position so that clear and meaningful characteristic values can be determined taking into account the direction dependency. In the case of an S-shaped pattern of the grinding grooves, the preferred roughness direction of which varies dependent on the radius, it is necessary to precisely determine the rotation angle of the optical sensor about its measuring axis dependent on the radius of the measuring position. Thus, in the invention, in a set-up mode the optical sensor is rotated at a predetermined measuring position about its measuring axis and an initial rotary position with associated initial rotation angle is determined, in which an intensity characteristic value is at a maximum. This intensity characteristic value is determined from signals of the photodetectors of the line sensor.

Typically, this intensity characteristic value is at a maximum whenever the longitudinal axis of the line sensor corresponds to the direction of the cross roughness. When the longitudinal axis of the line sensor corresponds to the direction of the cross roughness, then a large amount of the scattered-reflected intensity is incident on the line sensor and an intensity characteristic value is at a maximum. When, for example, the direction of the grinding grooves with respect to this longitudinal axis is rotated by 45°, then also the scattering indicatrix of the reflected scattered radiation is rotated by 45° with respect to this longitudinal axis of the line sensor and a part of the reflected radiation intensity is not incident on the photodetectors of the line sensor, which is reflected in a reduced intensity characteristic value.

After the initial rotation angle has been determined in the set-up mode, then in a measuring mode, characteristic values for the structure of the surface as well as shape features such as warpage, waviness, chatter marks, etc. are determined from the detected intensities of the photodetectors based on this initial rotation angle. As a characteristic value for assessing the surface quality, for example, the variance of the scattering angle distribution Aq can be used as a measure for the microstructure of the surface. For determining the waviness of the surface of the workpiece, the characteristic value M mentioned further above is calculated and its variation dependent on the rotation angle with which the workpiece is rotated in the rotary device is calculated. Further characteristic values are described in the mentioned VDA 2009.

The determination of the initial rotation angle can, for example, take place at a measuring position at the boundary of the workpiece, wherein the optical sensor is rotated about its measuring axis so far until the intensity characteristic value is at a maximum. Afterwards, the workpiece, for example a wafer, is rotated and the optical sensor continuously scans its surface on a circumferential circular path, and characteristic values with respect to the surface quality and their curves are determined. At various radii of the workpiece, each time the initial rotation angle can be determined dependent on the radius in the set-up mode so that a functional allocation of initial rotation angles to various radius values can be determined. When scanning the surface of the workpiece in the measuring mode, then dependent on the radial measuring position, the associated initial rotation angle is set.

The invention can be applied to differently machined workpieces. Preferably, the invention is applied to wafers which are fine-machined by grinding or polishing.

In one development of the method, a rotation angle resulting from the initial rotation angle plus a correction angle is set for the sensor. Preferably, the correction angle amounts to ±90° or ±45°. Since cross roughness and longitudinal roughness have a direction difference of 90°, given a rotation by ±90° once the cross roughness and once the longitudinal roughness and associated characteristic values, such as waviness or form deviation, can be determined. Using the correction angle of ±45°, intermediate values between longitudinal roughness and cross roughness are determined.

In one development of the method, the sum Ig of the intensities of all photodetectors of the line sensor is determined as an intensity characteristic value in the set-up mode. This value Ig is also necessarily determined in the calculation of the characteristic values for surface quality according to VDA 2009 so that this characteristic value is already available and easily finds a further use. Also the sum of the intensities of a smaller number of photodetectors can be used as an intensity characteristic value, as a result whereof the sum calculation can be accelerated.

According to a further aspect of the invention, a device for the contactless assessment of the surface quality of a disk-shaped, fine-machined workpiece is specified, with which the described method can be implemented. The advantages achievable by means of this device correspond to those of the previously described method.

Embodiments of the invention are explained in the following on the basis of the Figures.

FIG. 1 schematically shows the scattered light measuring principle for measuring the cross roughness.

FIG. 2a, b show the principle of back grinding and back polishing on wafers.

FIG. 4 shows a change of the scattered light distribution given a change in direction of the grinding grooves.

FIG. 11 shows a device in a block diagram.

Figure 2A:
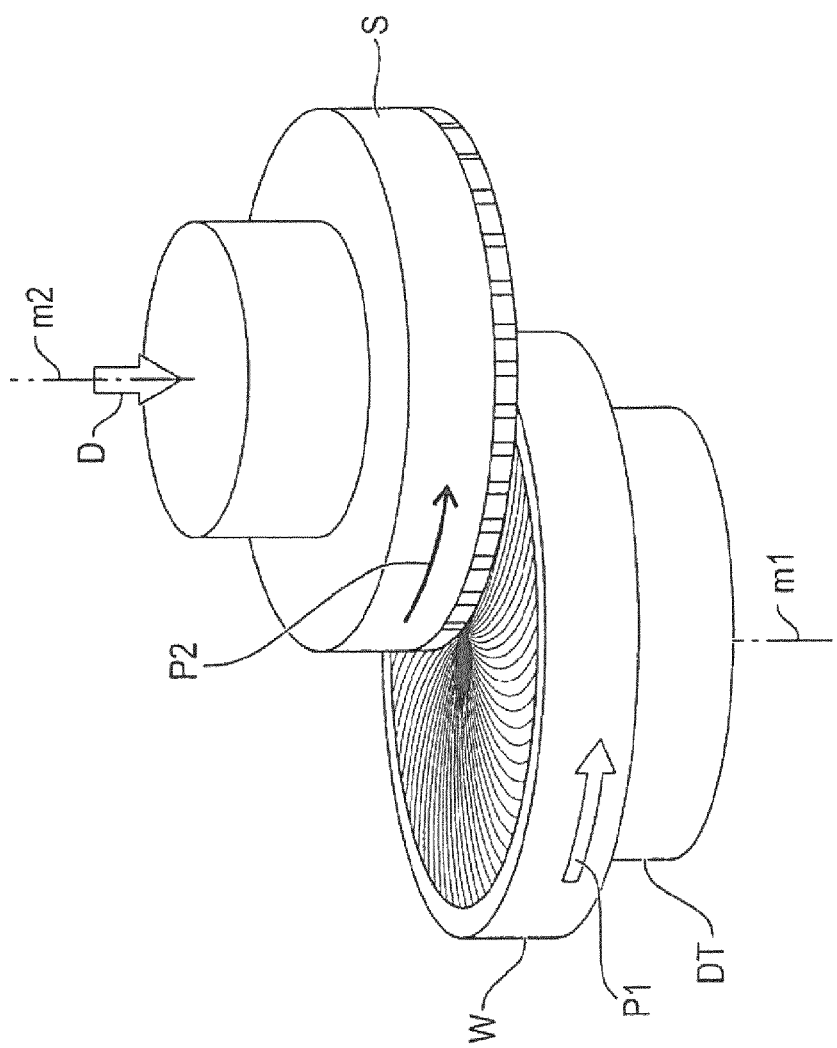

FIG. 1 schematically shows the measuring principle, as this is for example also described in the guideline VDA 2009 mentioned further above. An optical sensor 10 for the angle-resolved scattered light measurement comprises as a light source 12 an LED or a semiconductor laser that illuminates the surface O1 of a sample with a beam of rays of defined geometry and intensity distribution. On the surface, the beam of rays produces a measuring spot 14 which is approximately circular with a diameter d. The light re-scattered by the microstructure of the surface O1 is detected within the maximum measurable scattering angle range a by an optical measuring system O. A line sensor 16 comprising a discrete number of photodetectors 18 (only two photodetectors are identified) is arranged such that the individual photodetectors 18 convert, with respect to the discrete scattering angle values φ, the corresponding intensity values Iφ' into electrical signals that are further processed as digital values in a computer-aided control (not illustrated).

The optical measuring system O is designed as a Fourier optical system or f-theta optical system and transforms the scattering angles φ into a path φ' which corresponds to the position i of the individual photodetectors 18 along the line sensor 16. Thus, one obtains a distribution H1(φ') along the arrangement of photodetectors 18 with intensities Iφ'. By standardizing, the scattering angle distribution H(φ') of the microstructure in the measuring spot 14 can be calculated from this intensity distribution H1(φ').

The orientation of the sensor 10 with its measuring axis 20 is generally perpendicular to the surface O1 to be measured. In this case, the surface normal F1 of the surface O1 and the measuring axis 20 coincide. This measuring axis 20 in turn corresponds to a central axis or longitudinal axis of the sensor 10. When the surface normal F1 is tilted by an angle Δ1 with respect to the measuring axis 20 in the direction of the longitudinal axis 22 of the line sensor 16, then the intensity distribution H1(φ') is shifted by a value M1 with respect to the central position of the intensity distribution. This shift M1 can be used to determine, for example, errors in form (form deviations), waviness or an out-of-roundness of the surface O1. The value M1 corresponds to the first statistic moment of the scattering angle distribution curve H1(φ') with φ'=tan(φ) and thus to the center of area of this distribution curve H1(φ').

As a first statistic moment of a distribution curve H(φ'), M in general calculates to $$M = \Sigma \varphi' \cdot H(\varphi')$$

with $$H(\varphi') = I(\varphi')/\Sigma I(\varphi').$$

With respect to the discrete photodetectors i, M calculates to $$M = \Sigma_{i=1}^{n} (\varphi'i) \cdot Ii / \Sigma_{i=1}^{n} Ii,$$

where
i is the control variable from 1 to n,
n is the maximum number of photodetectors,
Ii is the measured intensity of the photodetector i, and
φ'i is the scattering angle assigned to the photodetector i.

The expression $\Sigma_{i=1}^{n} Ii$ characterizes the total intensity Ig that is incident on the photodetectors 18 of the line detector. This total intensity Ig, which emerges as a by-product in the calculation of M, is used as an intensity characteristic value in the set-up mode, as will be explained in more detail further below.

When calculating M, a standardization is performed which means that the characteristic value M is independent of the reflectivity of the surface of the workpiece. Based on the characteristic value M, also a fine adjustment of the sensor with respect to a surface normal of the surface to be measured can take place.

In the left part of the image of FIG. 1, the surface O1 has a stochastic grinding profile. In the right part of the image, a further surface O2 has an asymmetric roughness profile. Accordingly, there results a curve of the intensity distribution H2(φ') and, due to a tilt angle Δ2 of the surface normal F1 of the surface O2 with respect to the measuring axis 20 in the direction of the longitudinal axis 22 of the line sensor 16, there results a shifting of the scattered light distribution H2(φ') by M2.

Typical values for the sensor 10 are for the diameter d of the measuring spot 14 approximately 0.03 to 0.9 mm. The aperture angle α of the lens O is for example 32°. A corresponding number of photodetectors 18 is chosen such that there results a resolution for φ' of 1°. The number of measuring and calculation of characteristic values is greater than 1000/second.

In the angle-resolved scattered light method, one advantage is the insensitiveness with respect to variations in the distance, which may amount to up to 2 mm on plane surfaces.

An optical center OM of the sensor 10 lies on the measuring axis 20 in the area of the center of the lens O. In order to orient the sensor 10 in normal direction to the surface O1, O2, it is pivoted about the center OM until the characteristic value M is approximately 0 or minimal. From the intensity distribution H1(φ'), a plurality of characteristic values can be determined (see VDA 2009), such as the variance of the scattering angle distribution Aq as a measure for the microstructure of the surface, the characteristic value Aq* as a defect detection signal, e.g. for microcracks, the skewness of the scattering angle distribution Ask as a measure for the profile skewness of the microstructure and numerous other individual characteristic values and multiple characteristic values.

FIG. 2a shows an important application in which the workpiece is a wafer W, the back of which is thinned by grinding. The wafer W is arranged in a numerical machine tool (not illustrated) on a rotary table DT centrically with respect to the central axis m1 and rotates in arrow direction P1 when machined. A grinding wheel S on which pressure D is applied and which is tilted with its central axis m2 about the central axis m1 of the rotary table DT, rotates in arrow direction P2 and removes material from the back of the wafer W by machining. Due to the mutual rotation of wafer W and grinding wheel S, S-shaped grinding grooves are formed on the surface of the wafer W, which are partially still visible with the naked eye. The material removal shall be implemented such that the grinding forces are distributed on the surface of the wafer W as homogenously as possible, and the surface roughness resulting from the grinding process and the surface deformation shall be as little as possible so that the function of the ICs present in the wafer W is not affected.

Figure 2B:
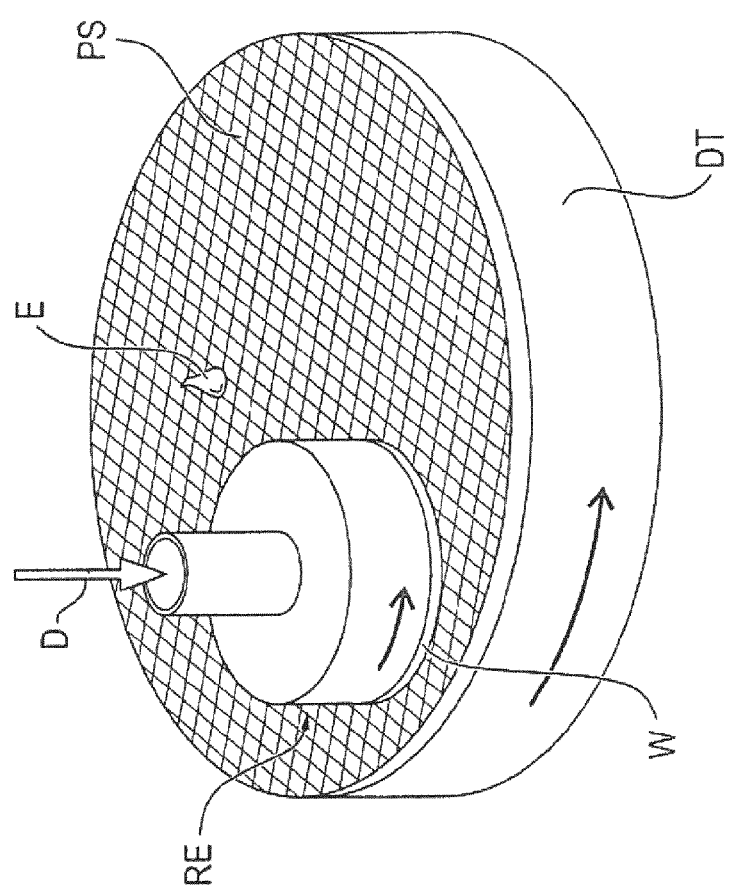

As already mentioned, FIG. 2b shows the CMP production process which effects a further leveling of the grinding structure. Due to the relative movement of wafer W and polishing wheel PS, a polishing pattern superimposes on the grinding pattern, which further complicates the nanotopography of the surface.

Figure 3:
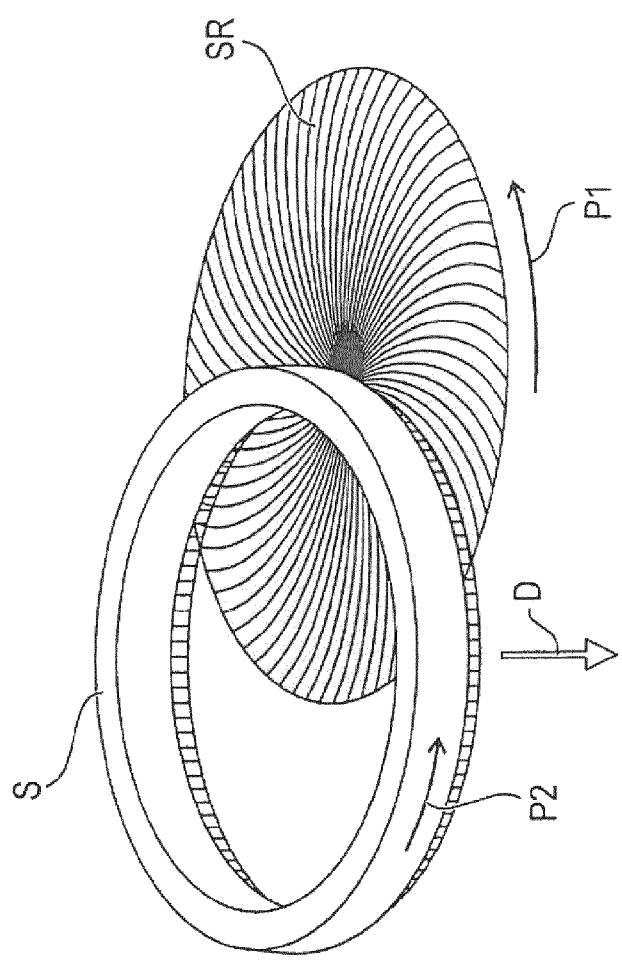
FIG. 3 shows grinding grooves on the wafer surface.

FIG. 3 shows in a further schematic illustration, the surface of the wafer W with S-shaped grinding grooves SR. When the rotation in direction P1 and P2 is exactly kept, the course of the grinding grooves is clearly defined as an analytic function and known from the set-up parameters for the numerical machine tool.

FIG. 4 schematically shows the measuring principle on a surface section for a surface O3 with grinding grooves extending in a straight manner in longitudinal direction L. At right angles thereto, the cross roughness is defined in cross direction Q. The reflected intensity of the radiation originates from the illuminated measuring spot 14, and is incident on the line sensor 16 in the plane E1 (or in the Fourier plane of the measuring lens O), which line sensor has been omitted for reasons of clarity. The scattered light distribution, in which the distribution H1 is included, has an elliptical structure in this plane E1, wherein the long semiaxis runs in cross direction Q and the short semiaxis runs in longitudinal direction L. When the longitudinal axis 22 of the line sensor 16 coincides with the long semiaxis of the scattered light distribution, then substantially the scattered light originating from the cross roughness is detected. In the right part of the image, the surface section O3 has been rotated anti-clockwise by a horizontal angle θ, which results in that in the case of an approximately perpendicular measuring axis 20 of the optical sensor 10 also the scattering light distribution rotates by this angle θ in the plane E1. Now, no longer the entire scattered light distribution associated to the cross roughness is detected along the longitudinal axis 22 of the line sensor 16 but only a part thereof. This in turn means that the characteristic values calculated from the measured intensities of the photodetectors 18 are not clearly related to the surface structure and contain measuring errors. In the practical application of the angle-resolved scattering light measuring technique, the characteristic values for roughness, error of form, waviness etc. are usually referred to the cross roughness or the longitudinal roughness.

Figure 5:
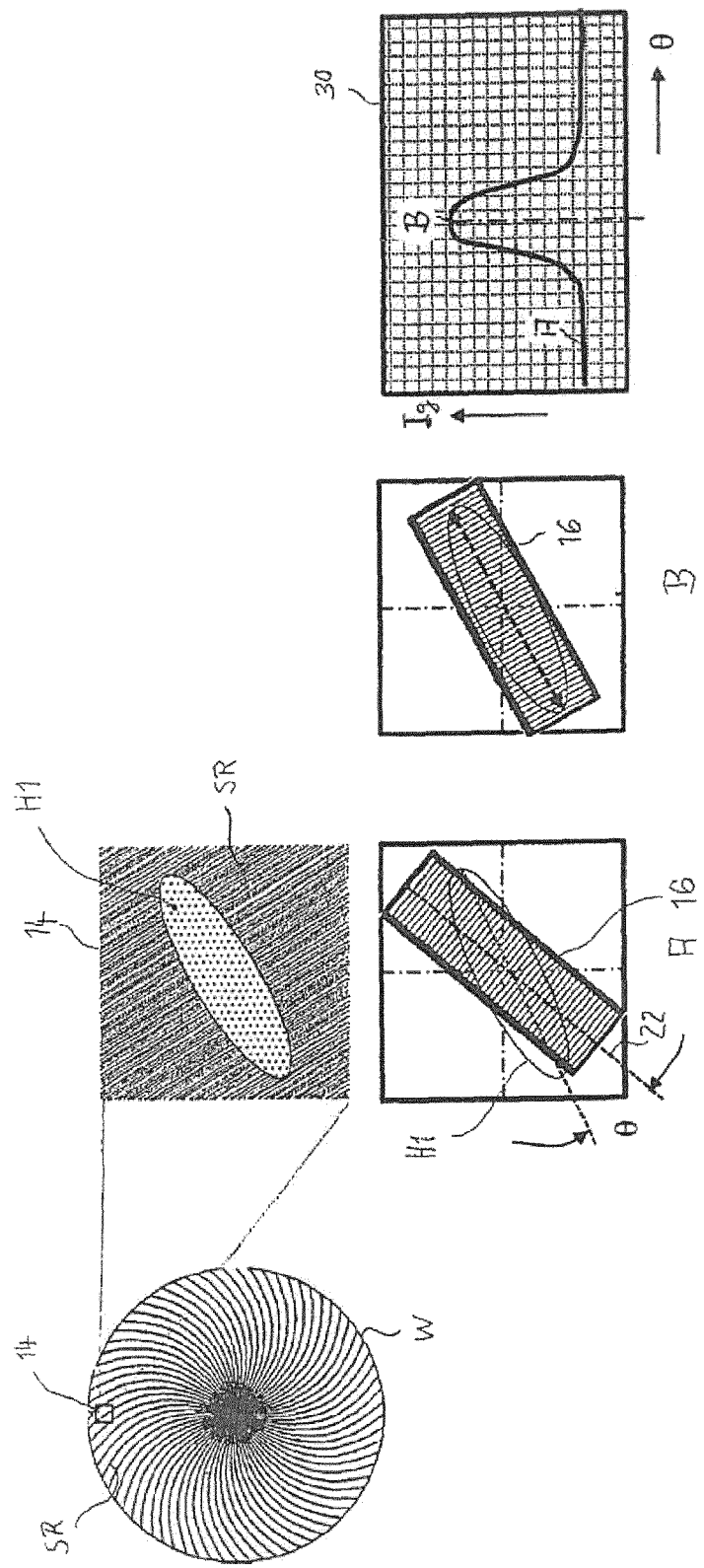
FIG. 5 shows a schematic determination of an initial rotation angle.

FIG. 5 shows in a schematic illustration the method used in the set-up mode for determining an initial rotation angle for the optical sensor 10. In the upper left part of the image, the top view of the surface of the wafer W with S-shaped grinding structure SR is illustrated. The optical sensor 10 is oriented with its measuring axis 20 perpendicular to the surface of the wafer W at a predetermined measuring position of the wafer W. The scattered light distribution H1 starting from the measuring spot 14 is illustrated in an enlarged detail with respect to the grinding grooves SR. As can be seen, the long semiaxis of the scattered light ellipse extend transversely to the direction of the grinding grooves.

In the lower image sections A and B, two states are illustrated. In state A, the optical sensor 10 with its line sensor 16 is rotated such that the longitudinal axis 22 of the line sensor 16 does not coincide with the long semiaxis of the elliptic scattered light distribution H1. To establish a correspondence, the line sensor 16 with its longitudinal axis 22 is to be rotated by an horizontal angle θ about the measuring axis 20. In state B, this is the case, and the intensity distribution H1 is completely detected by the photodetectors of the line sensor 16.

In the right part of the image, a diagram 30 is illustrated in which the intensity characteristic value Ig is entered as a sum of the intensities of all photodetectors 18 over the rotation angle θ. In the state B, where the long semiaxis of the elliptic intensity distribution H1 coincides with the longitudinal axis 22 of the line detector 16, the intensity characteristic value Ig is at a maximum. The associated initial rotation angle θ defines the initial rotary position for the optical sensor 10 in the predetermined measuring position. In radial direction of the surface of the wafer W, the initial rotation angle θ varies due to the S-shape of the grinding grooves.

Figure 6:
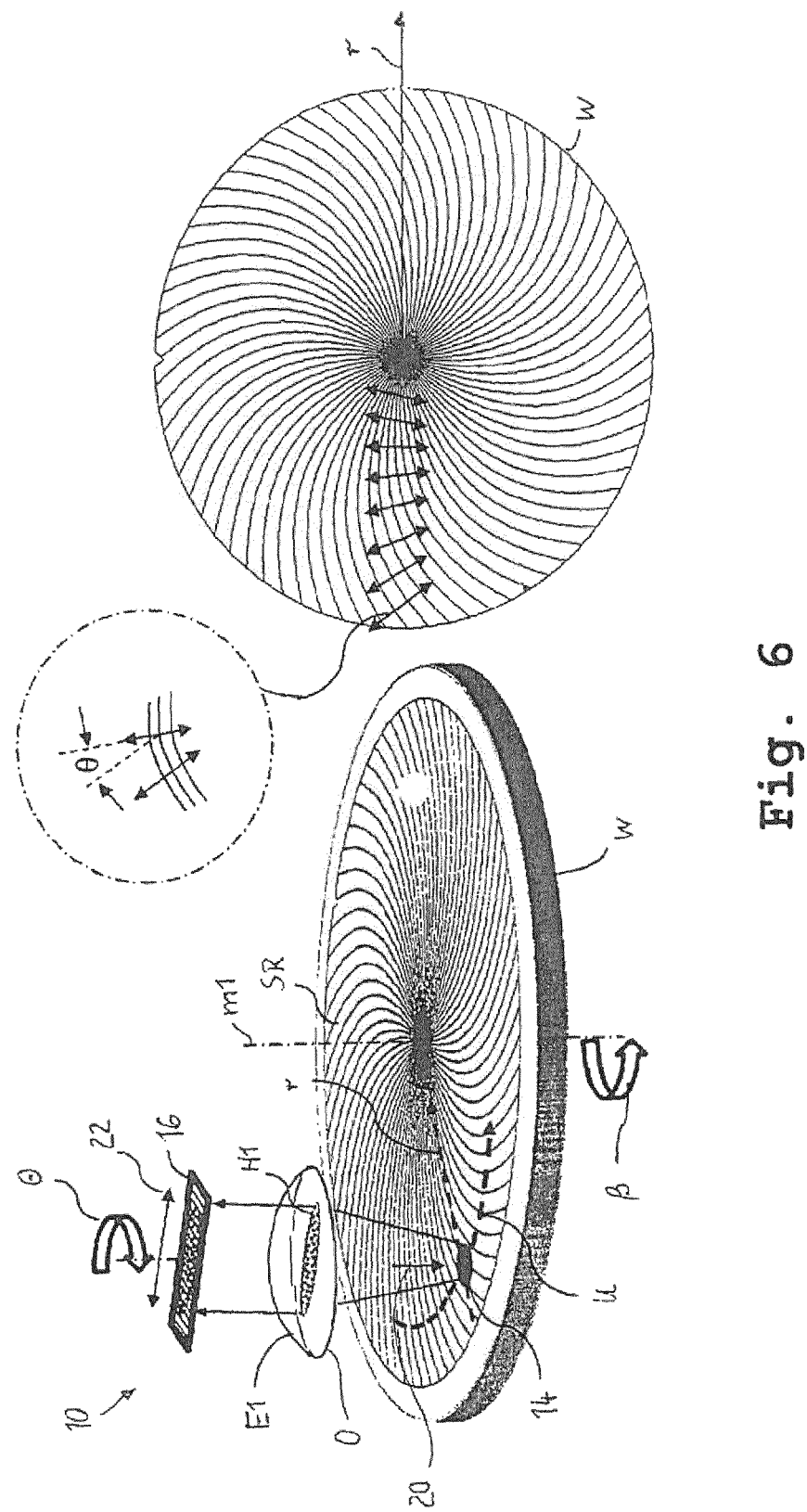
FIG. 6 shows the scanning principle for the surface of the wafer.

FIG. 6 shows in an illustration the scanning of the surface of the wafer W. The sensor 10 is oriented with its measuring axis 20 at a measuring position of the wafer W perpendicular to the surface and illuminates the measuring spot 14. The re-scattered radiation results in the intensity distribution H1 in the plane E1. As a result of the Fourier-optical imaging with the measuring lens O, the intensity distribution H1 is transformed into the plane of the line sensor 16. By rotating the sensor 10 about its measuring axis 20, the initial rotation angle θ is determined, in which the intensity characteristic value Ig is at a maximum. In the subsequent measuring mode, then the scanning of the surface of the wafer W takes place, wherein the wafer W is rotated by the rotation angle β about its axis m1. Upon each full rotation of the wafer W, the sensor 10 is moved by a small step in radial direction r to the axis m1. In general, the S-shape of the grinding grooves is known from the parameters of the back grinding and with regard thereto, there exists an analytic function F(r, θ). With every step, the sensor 10 is rotated such as a result of the known change of the groove direction of the S-shaped grinding grooves SR that the intensity distribution H1 is always fully incident on the line sensor 16 with its long semiaxis. In this way, the entire surface of the wafer W can be scanned. In the right part of the image of FIG. 6, for various radius values r it can be seen based on the double arrows how the longitudinal axis 22 of the line sensor 16 is to be oriented to detect the intensity distribution H1.

In the case of an unknown change of the grinding direction or the polishing direction, i.e. the exact S-shape of the grinding grooves SR is not known, an associated initial rotation angle θ can be determined for the associated radius value r at any measuring position on the surface of the wafer W. This initial rotation angle θ is then true for a certain circular path. For other radius values r, this procedure is to be repeated, or a check of the correct initial rotation angle θ may be performed. These processes normally run automatically. It is also possible to determine in a forerun-phase at different positions of the surface initial rotation angles corresponding to radius values and a function F(r, θ) by interpolation. This function F(r, θ) can then be used in the measuring mode to scan a section or the entire surface.

Figure 7:
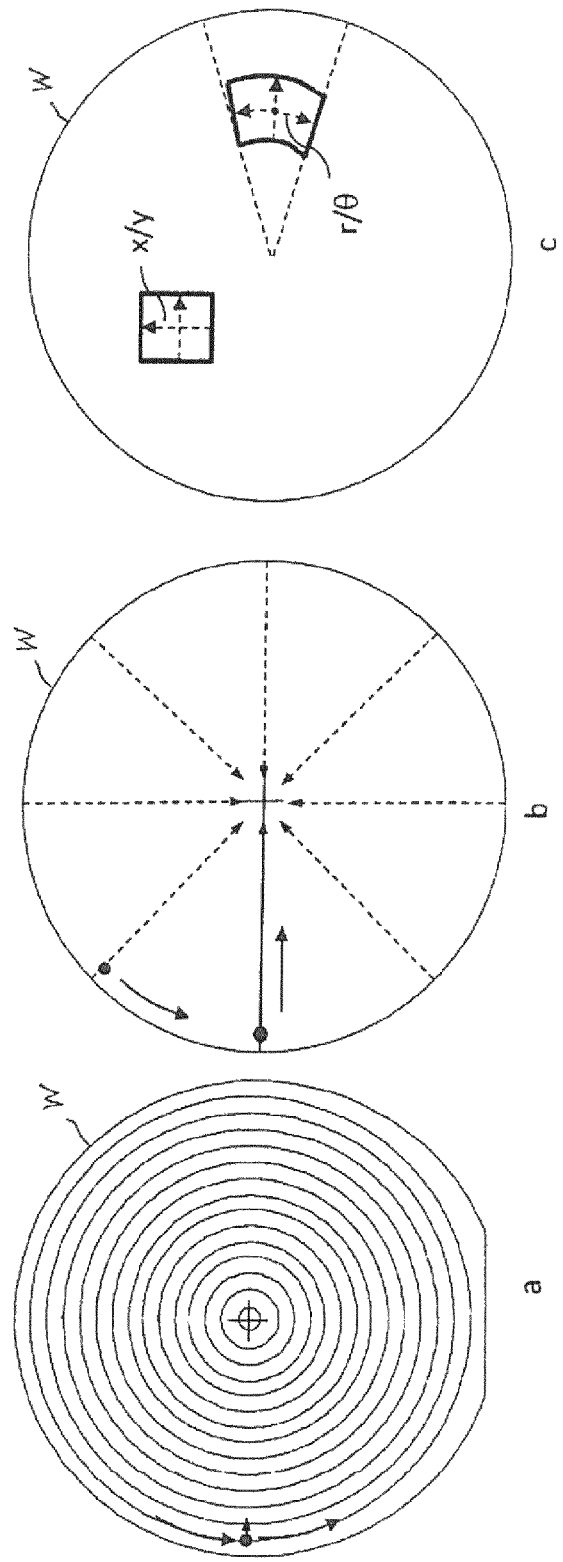
FIG. 7 shows various scanning strategies.

FIG. 7 shows different strategies when scanning the surface of the wafer W. According to illustration a, the scanning may take place in a circular manner starting from a specific measuring position. In illustration b, the scanning may take place in a star-shaped manner according to the direction arrows shown. In the illustration c, a scanning in the form of a segment of a circle may take place. If desired, also a scanning of a section with Cartesian coordinates x, y is possible.

Figure 8:
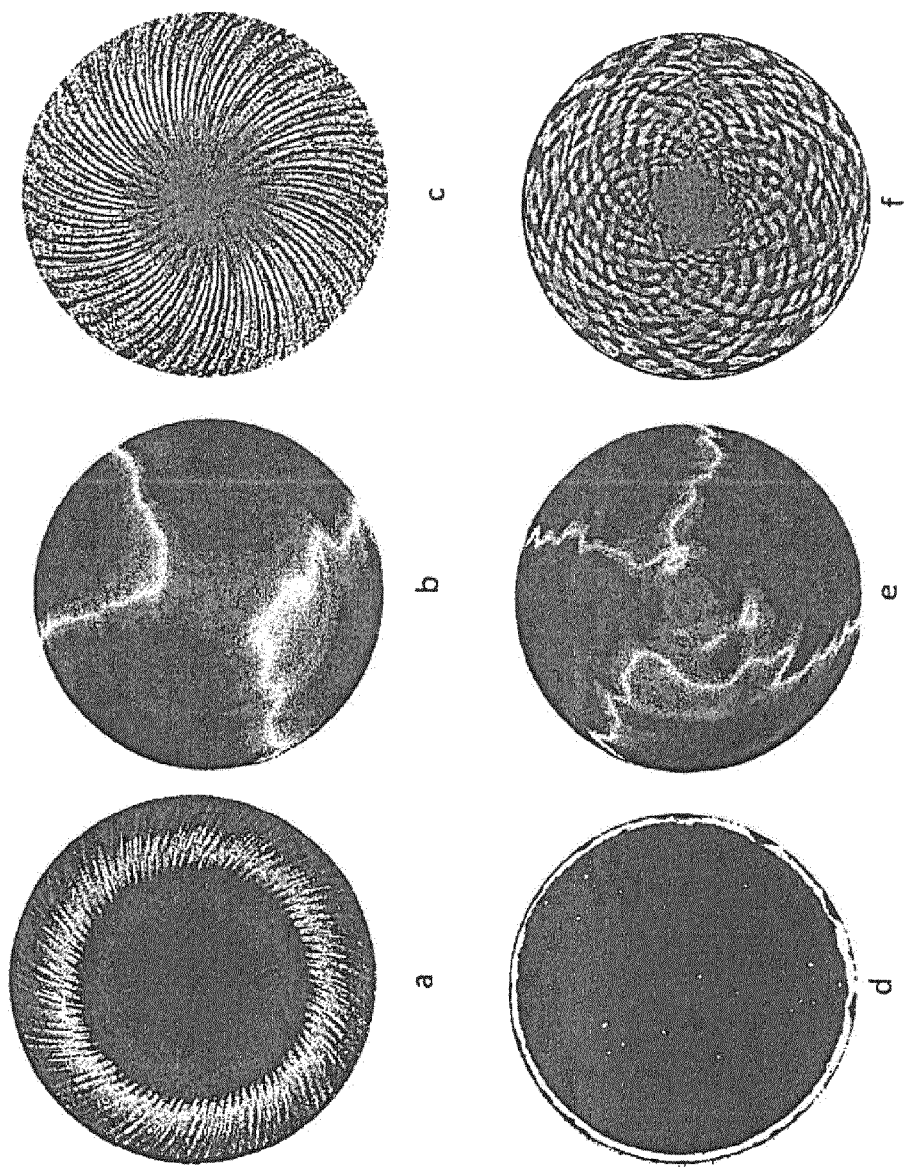
FIG. 8 shows an area-wise illustration of measuring results on wafers.

In FIG. 8, an illustration of measuring results is shown on two wafers W, each of which having a diameter of 300 mm. The wafer in the illustrations a-c has been ground, and the wafer in the illustrations d-f has additionally been polished. Each time, the scanning was done in a circular manner. In the illustration a and d, Aq values are illustrated measured over the entire surface. Bright areas show high Aq values, equivalent to increased roughness. Dark areas characterize low Aq values. It can be seen that in the boundary area of the wafer in illustration a, the Aq values are higher than in the middle and central area. The mean roughness values Ra fluctuate in the illustration a between 10-6 nm. In the illustration d (polished wafer) between 0.6-1.2 nm. In the illustrations b and e, errors of form in the macro range (warpage) are illustrated over the entire surface of the wafer W. Here, too, bright areas mean high warpage values and dark areas mean low warpage values. As viewed over the entire surface, the flatness or the warpage is in the illustration b in the range from −60 to +60 μm (peak to valley) and in the illustration e in the range from −10 to +10 μm. In the illustrations c and f, the waviness of the surface measured over the entire surface is illustrated as levels of grey. In the illustration c, it is in the range from −50 to +50 nm and in the illustration f, it is in the range from −5 to +5 nm. The improvement of the surface by the CMP method can clearly be seen (grey scale has been adapted). The roughness values Ra are based on a comparison measurement with a confocal measuring microscope, which, in the case of 1 nm, already operates at its lower tolerance limit. Also the form and the waviness were further improved by the CMP process. The measured waviness amplitudes are under 10 nm in the CMP process.

Figure 9:
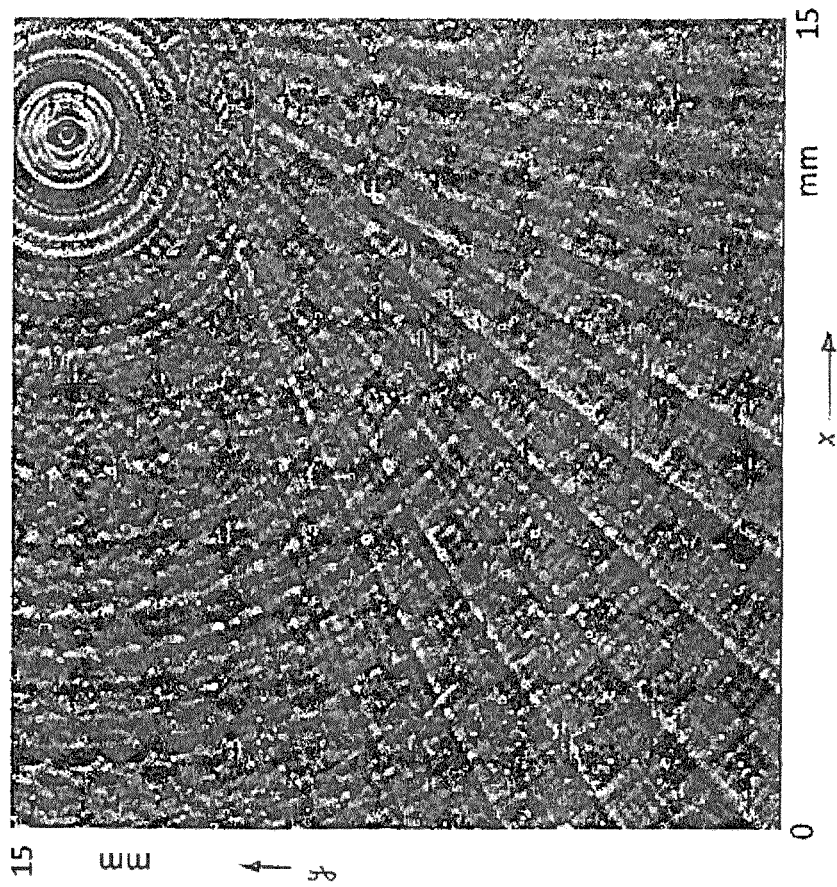
FIG. 9 shows results of waviness measurements on a CMP machined wafer surface.

FIG. 9 shows results of waviness measurements on a CMP machined wafer surface which had been obtained with a small measuring spot diameter of 30 μm and a scanning with a x/y scanning table. The radial structures that can be seen are remainders of the previous grinding and the circular structures are textures from the CMP machining. The amplitudes are under 10 nm.

Figure 10:
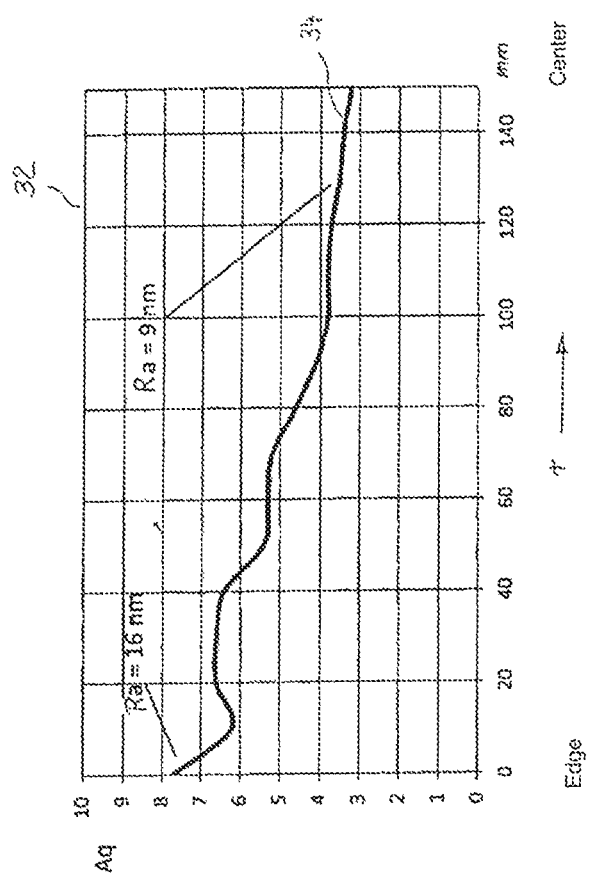
FIG. 10 shows measuring results Aq as a function of radius r.

FIG. 10 shows in a diagram 32 the curve of the roughness Aq of a ground wafer from the wafer edge (r=0) to the wafer center (r=140 mm). In the characteristic line 34 reference is, for example, made to the arithmetic mean roughness values Ra measured by a confocal microscope; they amount to 16 nm at the edge and 9 nm near the center.

FIG. 11 shows in a block diagram functional units of a device for performing the described method. The wafer W is arranged centrically on a rotary table 40 and is rotated by a rotary table control 42 by a rotation angle β, this rotation angle β being detected by a rotation angle sensor 44. A positioning device 46 positions the optical sensor preferably in x, y, z direction so that its measuring axis 20, which coincides with the central axis or longitudinal axis of the sensor 10, is perpendicular to the surface of the wafer W at a predetermined measuring position. Typically, the x axis runs in radial direction of the rotary table 40 so that x values correspond to radius values r of the wafer. The positioning device 46 mounts the sensor 10 rotatably about its measuring axis 20, as a result whereof a horizontal rotation angle θ can be set. Preferably, the rotary table 40 comprises a vacuum clamping device (not illustrated) which is connected to a vacuum pump and which holds the wafer W. In this way, a fast clamping and changing of a wafer W is possible.

A computer-aided control 50 controls the positioning device 46 as well as the rotary table 40, the various setting axes β, x, y, z, θ are adjusted by motors. The control 50 is also connected to the sensor 10 and evaluates its signals. The control 50 calculates the various characteristic values from these signals according to VDA 2009 and their curves over the rotation angle β and the radius r. The device is suitable for automatic surface testing in the laboratory and in the production of wafers. With the technology currently available, up to 10000 scattered light distributions per second can be detected by the line sensor and the associated characteristic values Ig, Aq and M for roughness, flatness and waviness be calculated. Higher scanning rates are to be expected in the future. In order to scan 100000 measuring positions on a wafer, one only requires 10 s, as a result whereof a comprehensive overall assessment of the wafer on the front and/or back is made possible. This is a considerable advantage of the method described herein. In addition, there is the extremely high lateral and vertical spatial resolution up into the subnanometer range.

LIST OF REFERENCE SIGNS 10 sensor
12 light source
14 measuring spot
D diameter of the measuring spot
O1 surface
α a maximally measurable scattering angle range
O measuring lens
16 line sensor
18 photodetectors
φ scattering angle values
Iφ' intensity values
H1(φ') intensity distribution
H(φ') scattering angle distribution
F1 surface normal
20 measuring axis
Δ1 angle
22 longitudinal axis of the line sensor
M1 shift with respect to the central position of the intensity distribution
O2 surface
H2(φ') intensity distribution
Δ2 tilt angle
M2 shift
Aq variance of the scattering angle distribution; roughness value
Ask profile skewness of the microstructure
Aq* defect detection signal
i running variable
Ii measured intensity of the photodetector i
Ig total intensity, intensity characteristic value
OM optical center of the sensor
W wafer
DT rotary table
m1 central axis of the wafer
P1, P2 arrow directions
D pressure
S grinding wheel
M2 central axis of the grinding wheel
RE rotation unit
PS polishing wheel
E emulsion
RA mean roughness value
SR grinding grooves
L longitudinal direction
Q cross direction
E1 level
θ horizontal rotation angle
r radius
30 diagram
32 diagram for the Aq value
40 rotary table 42 rotary table control
β rotation angle
44 rotation angle sensor
46 positioning device
50 control

The invention claimed is:

1. A method for the contactless assessment of the surface quality of a disk-shaped, fine-machined workpiece, in particular a wafer, according to the angle-resolved scattering light measuring technology,
in which an optical sensor emits a beam of rays with defined intensity distribution onto that surface of the workpiece which is to be assessed and illuminates a measuring spot,
the reflected intensity of the radiation is detected by means of a line sensor with a discrete number of photodetectors in a defined angular range and at least one characteristic value is determined therefrom,
the workpiece is rotatably mounted in a rotary device and the rotation angle is detected,
the sensor is oriented in a positioning device relative to the surface of the workpiece such that its measuring axis is perpendicular to the surface, wherein the positioning device mounts the sensor movably in radial direction relative to the surface of the workpiece) and rotatably about its measuring axis by an angle,
in a set-up mode, the sensor is rotated at a predetermined measuring position about its measuring axis and an initial rotary position with associated initial rotation angle is determined in which the intensity characteristic value is at a maximum,
and in which in a measuring mode, a control, taking into account this initial rotation angle, calculates from the detected intensity of the photodetectors at least one characteristic value for surface quality.

2. The method according to claim 1, characterized in that in the measuring mode, the control determines further characteristic values for surface quality, in which a rotation angle is set resulting from the initial rotation angle plus a correction angle.

3. The method according to claim 2, characterized in that the correction angle is ±45° or ±90°.

4. The method according to claim 1, in which in the set-up mode, the sum of intensities of several or all photodetectors of the line sensor is determined as intensity characteristic value.

5. The method according to claim 1, in which in the measuring mode, the rotary device rotates the workpiece by a predetermined angle and the sensor scans the surface of the workpiece continuously and the curve of the characteristic value or the characteristic values is determined along the associated circular path.

6. The method according to claim 1, characterized in that in the measuring mode, at least one section of the surface of the workpiece is area-scanned, wherein dependent on the radius of the measuring position on the workpiece, the rotation angle about the measuring axis of the sensor is changed.

7. The method according to claim 6, characterized in that the change of the rotation angle is accomplished according to a predetermined function.

8. The method according to claim 6, characterized in that the area-scanning takes place in a circular, partially circular, spiral-shaped or star-shaped manner.

9. The method according to claim 1, characterized in that the illuminated measuring spot has a diameter of 20 to 300 μm.

10. A device for the contactless assessment of the surface quality of a disk-shaped, fine-machined workpiece, in particular a wafer, according to the angle-resolved scattering light measuring technology, comprising
an optical sensor which emits a beam of rays with defined intensity distribution onto the surface of the workpiece to be assessed and illuminates a measuring spot,
wherein the reflected intensity of the radiation is detected by means of a line sensor with a discrete number of photodetectors in a defined angular range and at least one characteristic value is determined therefrom,
a rotary device which rotatably mounts the workpiece, wherein a rotation angle sensor detects the rotation angle,
a positioning device which orients the sensor relative to the surface of the workpiece such that its measuring axis is perpendicular to the surface, wherein the positioning device mounts the sensor movably in radial direction relative to the surface of the workpiece and rotatably about its measuring axis by an angle,
wherein in a set-up mode, the sensor is rotated at a predetermined measuring position about its measuring axis and an initial rotary position with associated initial rotation angle is determined in which the intensity characteristic value is at a maximum,
and wherein in a measuring mode, a control, taking into account this initial rotation angle, calculates from the detected intensity of the photodetectors at least one characteristic value for the surface quality.

11. The device according to claim 10, characterized in that in the measuring mode, the control determines further characteristic values for the surface quality, wherein a rotation angle is set resulting from the initial rotation angle plus a correction angle.

12. The device according to claim 11, characterized in that the correction angle is ±45° or ±90°.

13. The device according to claim 10, in which in the measuring mode, the rotary device rotates the workpiece by a predetermined angle and the sensor scans the surface of the workpiece continuously and the curve of the characteristic value or the characteristic values is determined along the associated circular path.

14. The device according to claim 10, characterized in that in the measuring mode, at least a section of the surface of the workpiece is area-scanned, wherein dependent on the radius of the measuring position on the workpiece the rotation angle about the measuring axis of the sensor is changed.

15. The device according to claim 10, characterized in that the illuminated measuring spot comprises a diameter of 20 to 300 μm.

* * * * *